(12) United States Patent
Richart

(10) Patent No.: US 11,518,582 B2
(45) Date of Patent: Dec. 6, 2022

(54) PACKAGING AND CORRESPONDING UNPACKAGING PROCEDURE

(71) Applicant: SELENIUM MEDICAL, La Rochelle (FR)

(72) Inventor: Olivier Richart, Le Bois Plage en Ré (FR)

(73) Assignee: SELENIUM MEDICAL, La Rochelle (FR)

( * ) Notice: Subject to any disclaimer, the term of this patent is extended or adjusted under 35 U.S.C. 154(b) by 317 days.

(21) Appl. No.: 16/838,605

(22) Filed: Apr. 2, 2020

(65) Prior Publication Data
US 2020/0317408 A1    Oct. 8, 2020

Related U.S. Application Data

(60) Provisional application No. 62/828,841, filed on Apr. 3, 2019.

(30) Foreign Application Priority Data

Apr. 3, 2019 (FR) ...................................... 1903587

(51) Int. Cl.
*B65D 43/26* (2006.01)
*B65D 43/18* (2006.01)
(Continued)

(52) U.S. Cl.
CPC .............. *B65D 43/26* (2013.01); *A61B 50/30* (2016.02); *B65D 43/18* (2013.01); *B65D 53/00* (2013.01);
(Continued)

(58) Field of Classification Search
CPC ...... B65D 43/265; B65D 43/26; B65D 43/18; B65D 43/16; B65D 43/14; B65D 53/00; A61B 50/30
(Continued)

(56) References Cited

U.S. PATENT DOCUMENTS 5,031,768 A * 7/1991 Fischer .................. A61B 50/33
 206/370
5,096,114 A * 3/1992 Higginbotham ....... A61B 50/36
 229/149
(Continued)

FOREIGN PATENT DOCUMENTS

FR         2959216 A1   10/2011
WO   2018/065733 A1    4/2018
(Continued)

OTHER PUBLICATIONS

French Search Report and Written Opinion issued in International Patent Application No. PCT/FR2020/000080, dated Oct. 5, 2020, 9 pages.
(Continued)

*Primary Examiner* — Robert J Hicks
(74) *Attorney, Agent, or Firm* — Brown Rudnick LLP; Thomas C. Meyers

(57) ABSTRACT

The invention relates to a package comprising a hollow body, a lid joined to the hollow body by a hinge, and a protective cover (that can be moved between a closed position in which it covers the lid and an open position in which it is separated from the hollow body and forms, with a coupling device, a lever arm coupled to the lid, with the coupling device being able to assume a retracted configuration when the cover is in the closed position, and a deployed configuration when the cover is in the open position. The invention also relates to a corresponding unpackaging process.

21 Claims, 16 Drawing Sheets

(51) Int. Cl.
  *A61B 50/30* (2016.01)
  *B65D 53/00* (2006.01)
  *A61B 50/00* (2016.01)
(52) U.S. Cl.
  CPC . *A61B 2050/006* (2016.02); *A61B 2050/0066* (2016.02)
(58) Field of Classification Search
  USPC ... 220/212.5, 212, 315, 254.9, 254.1, 259.5, 220/256.1, 264, 263, 262, 260; 53/492
  See application file for complete search history.

(56) References Cited

U.S. PATENT DOCUMENTS

| | | | |
|---|---|---|---|
| 5,235,795 A * | 8/1993 | DeBusk | A61B 50/13 414/403 |
| 2018/0273274 A1* | 9/2018 | Ho | A47J 41/00 |

FOREIGN PATENT DOCUMENTS

| | | |
|---|---|---|
| WO | 2018/078242 A1 | 5/2018 |
| WO | 2019/030451 A2 | 2/2019 |
| WO | 2019/220067 A1 | 11/2019 |

OTHER PUBLICATIONS

French Search Report issued in French Patent Application No. 1903587, dated Dec. 5, 2019, 2 pages.

\* cited by examiner

PACKAGING AND CORRESPONDING UNPACKAGING PROCEDURE

CROSS-REFERENCE TO RELATED APPLICATIONS

This application claims priority to, and the benefit of, U.S. Provisional Application No. 62/828,841, filed Apr. 3, 2019, and French Application No. FR 19 03587, filed Apr. 3, 2019, the contents of each of which are incorporated by reference herein in their entireties.

FIELD OF INVENTION

This invention generally relates to a package for objects, in particular for medical parts that preferably have been sterilized.

PRIOR ART

International application WO2018078242A1, the content of which is incorporated as a reference into the present application, describes a package comprising a lower shell and an upper shell.

The upper shell comprises a connecting part that is bonded to the lower shell and a part forming a lid that is joined to the connecting part by a hinge. A sealing strip is affixed to the edges of the slot defined between the lid and the connecting part.

The package also comprises a protective cover that enables the sealing strip to be covered. The operator can remove the cover to pull off the sealing strip.

When the sealing strip has been pulled off, the mobility of the hinge on the upper shell is enabled such that the operator can pivot the lid of the upper shell in order to remove the contents of the package.

It is nevertheless desirable to further improve such a package to make it easier to use by the operator.

SUMMARY OF THE INVENTION

To this end, the invention relates to a package capable of containing an object, said package being comprised of:
a hollow body with an outlet opening for said object;
a lid joined to the hollow body by a hinge, enabling the hollow body to be closed,
a protective cover,
in which said package also comprises a coupling device between the protective cover and the lid,
said protective cover being movable between:
a closed position in which it covers the lid and in which the coupling device assumes a contracted configuration, and
an open position in which it is separated from the hollow body and in which the coupling device assumes a deployed configuration,
with the protective cover forming with the coupling device, in said open position, a lever arm coupled to the lid.

The package can also include one or more of the following characteristics used in any technically permissible combination.

According to an advantageous feature of the invention, said package includes a closure system, removable, defeasible, or breakable, allowing to keep the lid in the position of closing the hollow body.

According to an advantageous feature of the invention, the package includes a sealing strip that is applied to the edges of a defined slit between the lid and the hollow body.

According to an advantageous feature of the invention, with the hinge having an axis and the hollow body having an axis of exit of said object through said opening, the connection device is rigid with respect to a force applied transversally to the axis of exit of the hollow body and transversally to the axis of the hinge, to allow the lid to rotate.

According to an advantageous feature of the invention, the coupling device comprises a fastening system designed to hold the coupling device in the retracted configuration, for example folded or contracted, when the protective cover is in the closed position, while enabling said fastening system to be disabled when the protective cover is moved from said closed position to said open position, which causes the coupling device to assume the deployed configuration.

According to an advantageous feature of the invention, the coupling device comes in the form of a body with a deformable closed outline, preferably plastic, by traction.

According to an advantageous feature of the invention, the coupling device consists of two arms, each arm having an elbow.

According to an advantageous feature of the invention, each arm has a thinning of material at the elbow level. According to a particular aspect, thinning is also provided between the arms and ties.

According to an advantageous feature of the invention, each arm has a hooking system configured to hold one against the other the two arm portions which extend on either side of the elbow in the folded position of the arm.

According to an advantageous feature of the invention, each arm has a hooking device configured, in cooperation with a corresponding hooking device on the lid, to keep said arm coupled to the lid in retracted configuration of the coupling device.

According to an advantageous feature of the invention, the two arms being connected by a lower and upper crossbars, the support system comprises a male part formed on one of the crossbars and a female part formed on the other crossbar, said male and female parts being configured to work by snap-fastening with one another in the closed position of the protective cover.

According to an advantageous feature of the invention, the lid has an insertion housing configured to receive and maintain a part of the coupling device in relation to the lid.

According to an advantageous feature of the invention, said package comprises a coupling system for the coupling device to the lid, the coupling system being configured so that, in the deployed state of the coupling device, the coupling device may be pivoted in relation to the lid so as to be able to bring the edge of the opening of the cover resting on the lid.

According to an advantageous feature of the invention, the protective cover comprises two cover parts that are assembled to enable a part of the coupling device to be mounted to the insert housing of one of the cover parts by a lateral opening in said cover part, and to close said lateral opening by means of the other cover part.

According to an advantageous feature of the invention, the package houses an interior package containing an object.

According to an advantageous feature of the invention, the package houses a gripping device to which the object is coupled.

The invention also concerns a process of deconditioning an object housed in a package as described above, in which said process includes the following steps:

moving the protective cover to the open position, with the protective cover remaining joined to the lid by the coupling device;

the application of a force on the protective cover to cause the lid to pivot around the axis of the hinge.

According to an advantageous feature of the invention, said process also includes, between those steps of moving the protective cover and applying an effort on the protective cover to rotate the lid, a rotating step of the protective cover to bring the edge of the opening of the protective cover resting on the lid.

According to an advantageous feature of the invention, the process also includes, after the removal stage of the protective cover, a step of removal of a sealing strip applied to the edges of a defined slit between the lid and the first hollow body.

According to an advantageous feature of the invention, the process also includes a step of separation of the lid from the hollow body by applying a pulling or twisting effort on the lid and/or the protective cover.

According to an advantageous feature of the invention, the protective cover is separated from an access to said hollow body by pivoting or removing the lid and cover assembly from the hollow body.

BRIEF DESCRIPTION OF THE DRAWINGS

Other characteristics and advantages of the invention will also be highlighted in the following description, which is purely illustrative and non-limiting and which must be read in relation to the appended drawings, of which.

DETAILED DESCRIPTION

Figure 1:
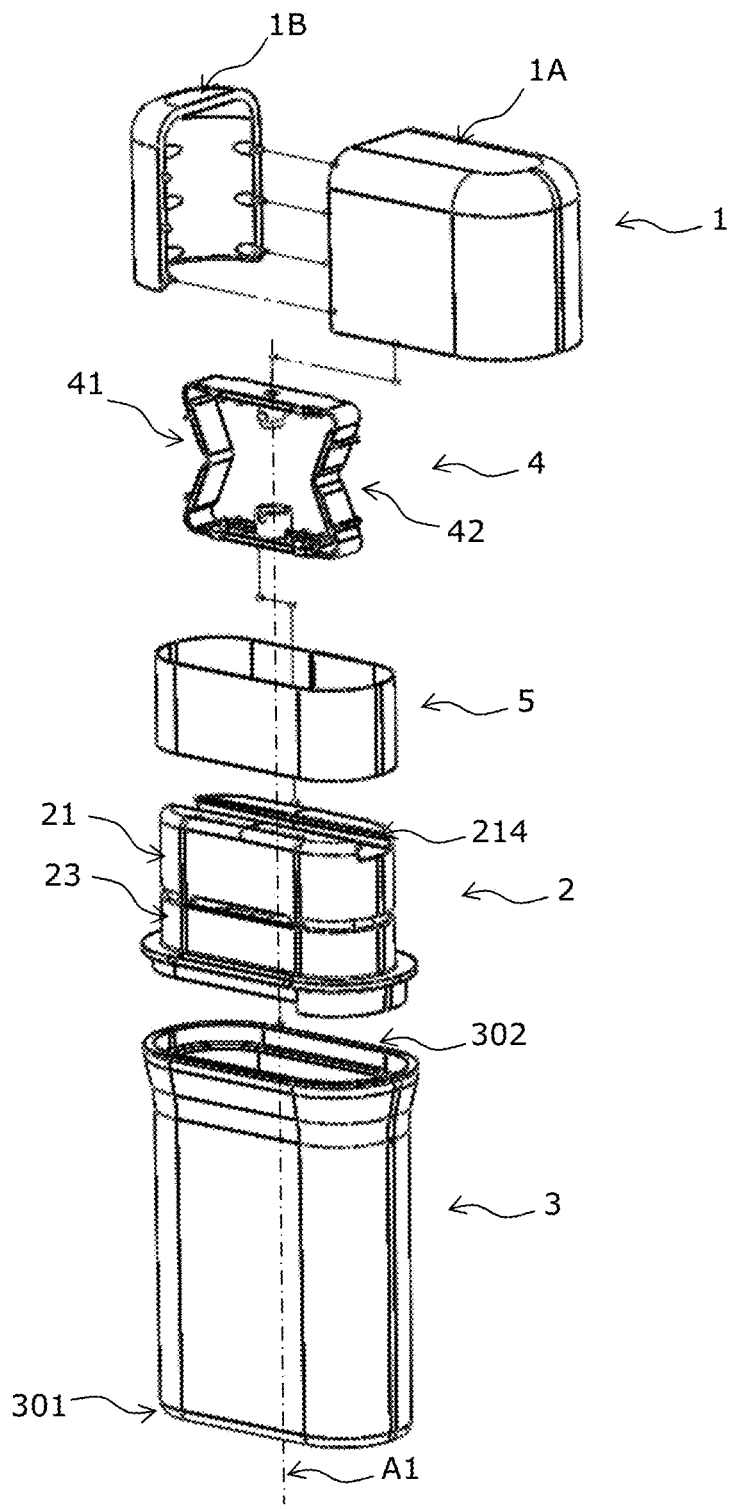
FIG. 1 is an exploded view of a package according to one embodiment of the invention, with the coupling device shown in the deployed position.

The inventive concept is described in more detail hereafter, with reference to the attached drawings, wherein embodiments of the inventive concept are shown. Like numbers refer to like elements in all of the drawings. However, this inventive concept can be implemented in many different forms and should not be interpreted as being limited to the embodiments described herein. Rather, these embodiments are proposed in order to provide a complete description and convey the extent of the inventive concept to those skilled in the art. Therefore, the extent of the invention is defined by the attached claims. For the sake of simplification, the following embodiments are examined in relation to the terminology and structure of a package.

Throughout the specification, reference to "an embodiment" means that any particular function, structure, or characteristic described in relation to an embodiment is included in at least one embodiment of the present invention.

Thus, the appearance of the expression "in an embodiment" in various places throughout the specification does not necessarily refer to the same embodiment. Moreover, the particular functions, structures, or characteristics can be combined in any appropriate way in one or more embodiments.

According to the embodiments and more in particularly in reference to FIGS. 1 to 15, a package 6 comprising a lower shell 3 and an upper shell 2 is proposed. Likewise, another embodiment is proposed in FIGS. 16 to 27A, which proposes package 66 using a part of the components of the embodiment of FIG. 1 and presenting modifications on other components. Thus, the lower shell 3, the sealing strip 5, and the lower part 23 of the upper shell 62 may be identical or similar in the embodiment of FIGS. 1 and 16, so that the same reference numbers are assigned to them. However, as detailed below, the lid 621 of the upper shell 62, the coupling device 64, and the cover 61 of the embodiment of FIG. 16 differ from the corresponding components 21, 4, and 1 of the embodiment of FIG. 1.

The description below of the package 6 in connection with the embodiment of FIGS. 1 to 15 can be applied to the package 66, except, of course, with regard to the elements of the package 66 which differ from those in the package 6. In particular, the description made for the lid 21 can also apply to the lid 621, except as regards the groove 214 of the lid 21 which, for the lid 621, is replaced by the coupling elements 6214, 6217. Similarly, the description of the coupling device 4 can also apply to the coupling device 64, except for the coupling system of the coupling device 64 to the lid 621, which differs from the coupling system of the coupling device 4 to the lid 21. Likewise, the coupling of the coupling device 64 to the lid 61 differs from that of the coupling device 4 to the lid 1 and the arms of the coupling device 4 are distinguished from those of the coupling device 64.

According to one embodiment, the lower shell 3 and/or the upper shell 2 are made of a translucent material that is preferably transparent.

The upper shell 2 comprises a connecting part 23 and a lid 21 that are joined by a hinge 22. According to one embodiment, the lid 21, the hinge 22 and the connecting part 23 of the upper shell 2 are formed in one piece, preferably of plastic. The hinge 22 can be formed by means of a simple junction between the lid 21 and the connecting part 23. According to a particular aspect, the hinge can be broken by twisting and/or pulling.

Each shell is considered to be an open shell, meaning that it forms a blind cavity and, when assembled to the other, enables a closed chamber to be defined when a sealing strip has been affixed over the lid 21 and the connecting part 23, as detailed below.

In the example shown in the drawings, the sealing strip forms a closure system that prevents access to the interior of the hollow body. The following description of a sealing strip also applies to other types of closure systems. Thus, as an alternative, the closure system can be adhesive or a weld applied to an area between the lid and the hollow body, or the closure system can be a junction that has been weakened, for example by scoring, between the lid and the hollow body. In these alternatives, the closure system can be undone or broken when the lid is pivoted around the hinge axis.

Thus, when in a closed position, the protective cover 1 covers the lid 21 and conceals the closure system. When the protective cover 1 is in an open position, the closure system is accessible. When the lid 21 is covered by the cover 1, the lid 21 extends at least partially, and preferably completely, into the interior of the cover. When the protective cover 1 is in the open position, the lid 21 is less, or not at all, extended into the interior of the cover 1 than when the cover 1 is in the closed position.

The package 6 can contain another package, referred to as an inner package. The inner package can contain a medical implant. The inner package and the outer package then form a double package.

As an alternative, the inner package can be devised to contain an object other than a medical implant. The inner package can contain (an)other medical part(s) that preferably has (have) been sterilized.

Figures 14, 15:
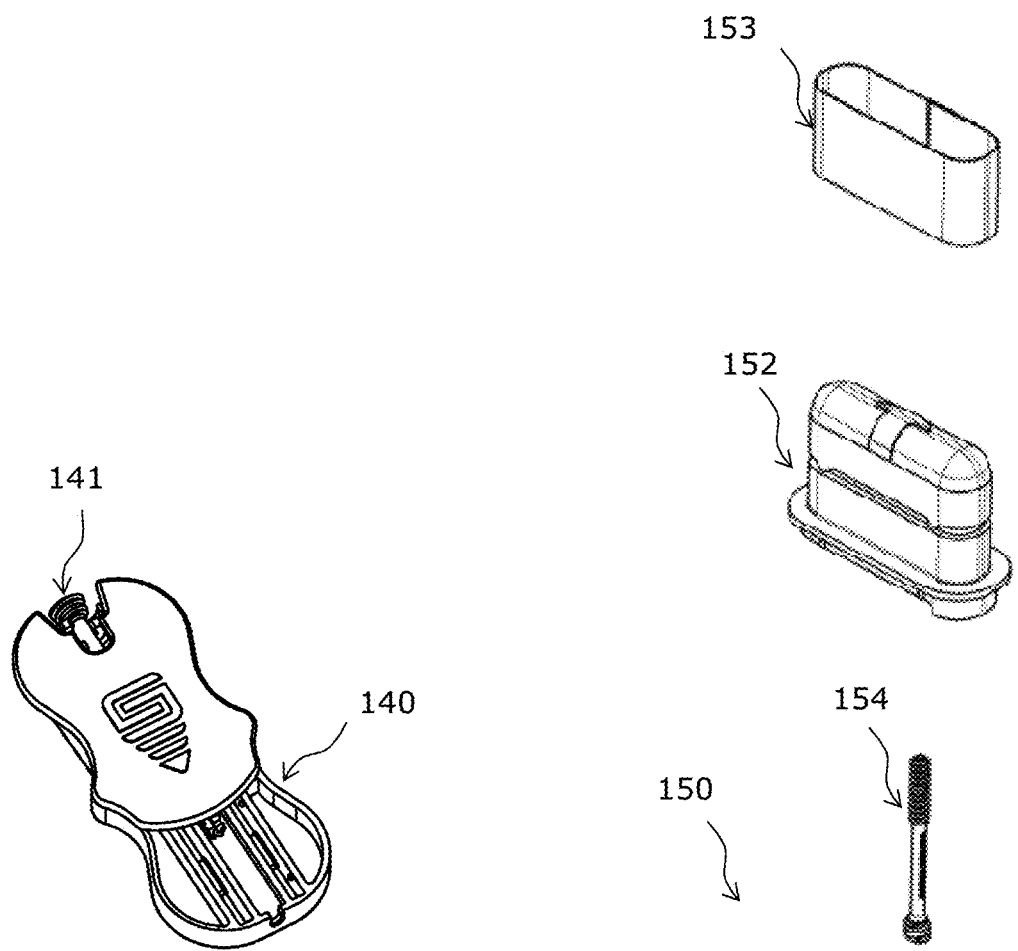
FIG. 14 is a perspective view of an example of a gripper, to which is coupled an object, which can be contained in a package according to the invention.
FIG. 15 is an exploded view of inner an package containing an object; said inner package can be contained in an (outer) package according to the invention.

As shown in FIG. 15, which shows an inner package 150, the inner package can comprise a lower shell 151 and an upper shell 152 to which a sealing strip 153 has been affixed in a manner similar to that of the package 6, which is then considered to be the outer package. The inner package 150 contains an object such as a medical screw 154.

In particular, the inner package can be similar or identical to an inner package as described in international application WO2018078242A1, the content of which is incorporated as a reference into the present application, or in international application WO2019030451A2, the content of which is incorporated as a reference into the present application. According to an alternative embodiment, the inner package can be devised to be similar or identical to the package equipped with the coupling device described in the present application, with dimensions adapted to fit into the outer package.

Figure 16:
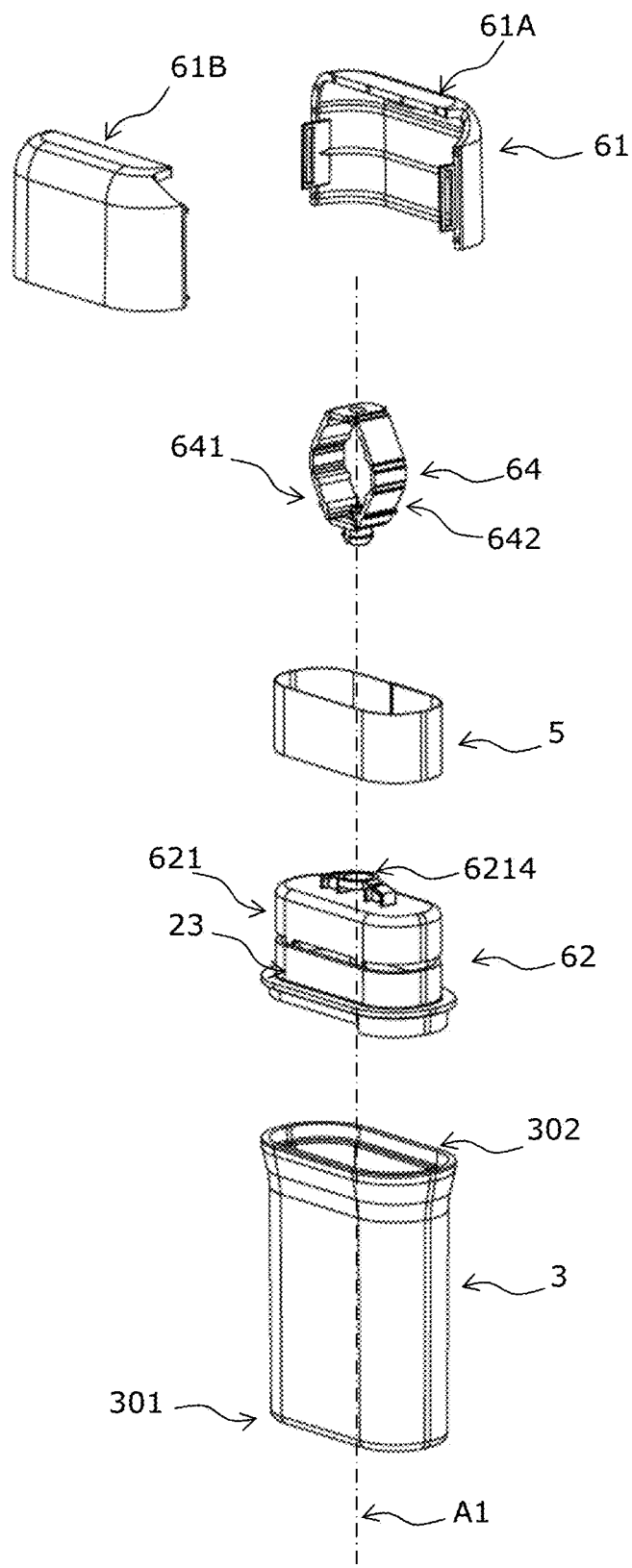
FIG. 16 is an exploded view of a package according to another embodiment of the invention, with the coupling device shown in the deployed position.

As an alternative, as shown more specifically in FIG. 16, the outer package can also be devised to accommodate a gripper 140 (or system for holding an object) attached to an object, such as a medical screw 141.

As an example, the gripper (or system for holding an object) can be similar or identical to the one(s) described in international application WO2018065733A1, the content of which is incorporated as a reference into the present application, or in international application WO2019030451A2, the content of which is incorporated as a reference into the present application, or in international application WO2019220067A1, the content of which is incorporated as a reference into the present application.

The package 6 can also be devised to directly accommodate a desired object, such as one or more medical part(s), with no inner package or intermediate gripper.

The object can be, for example, a solid part, such as a surgical screw, or any other type of object, particularly any other type of implant. Moreover, said object can be a liquid or a powder. Said object and, preferably, the various parts of the package, are sterilized, for example by radiation.

The package (or the double package) is designed to preserve the sterility of said object with a view to unpacking the object under aseptic or near-aseptic conditions.

Lower Shell

The lower shell 3 is in the form of a hollow body with a closed extremity forming the bottom 301 and an opposite extremity 302 that is open. According to a particular aspect detailed hereafter, the rim of the extremity 302 is attached to the connecting part 23 of the upper shell.

The lower shell 3 can be similar or identical to the one described in application WO2018078242A1, the content of which is incorporated as a reference into the present application.

Upper Shell

The upper shell 2 can also be similar or identical to the one described in application WO2018078242A1, the content of which is incorporated as a reference into the present application, with the difference being that the lid 21 of the upper shell 2 is coupled to the coupling device 4. To this end and as proposed in the example shown in the drawings, the upper portion 10A of the lid 1 can be equipped with a specific system for receiving the coupling device 4.

The connecting part 23 of the upper shell 2 is in the form of a through body. In particular, the connecting part 23 is in the form of a section of the upper shell. The connecting part 23 can be devised to have a generally cylindrical shape.

The hinge 22, which joins a portion of the upper rim of the connecting part 23 to the rim of the lid 21, enables the lid 21 to be articulated in relation to the connecting part 23 between a raised (open) position allowing access to the interior of the connecting part 23 and a lowered (closed) position preventing access to the interior of said connecting part 23.

According to a preferential aspect, when assembled, said connecting part 23 of the upper shell 2 and the lower shell 3 form two parts attached to each other such that they cannot be disassembled by the user. The lower rim of the connecting part 23 is nested in a flared portion of the extremity of the lower shell 3. The lower shell 3 is bonded to the connecting part 23, for example by welding. Preferentially, the bond is achieved by welding between a flange on the connecting part 23 and the rim of the extremity 302 of the lower shell 3.

When the lid is in the closed position, the rims of the lid 21 and of the connecting part 23 are facing each other and together form said upper shell.

When the lid 21 is in the closed position, it defines with the connecting part 23 a slot 20 (which is visible in particular in FIG. 8) that extends from one extremity of the hinge 22 to the opposite extremity of said hinge 22.

In the examples shown in the drawings and as recalled above, the connecting part 23 is bonded to the lower shell 3 such that the assembly of the connecting part 23 and the lower shell 3 forms a hollow body, also referred to as the main hollow body, in which an object can be accommodated. As an alternative, the main hollow body can be devised to be formed in one piece.

Axis A1 is defined as the exit axis of the object (out of the main hollow body), i.e., the central axis of the opening 230 of the connecting part 23. When the lid 21 is in the closed position, this axis A1 also corresponds to the normal at the orifice of the cover 1.

Furthermore, in the example shown in the drawings, this axis A1 corresponds to the longitudinal axis of the package.

The main hollow body thus has an opening at one of its extremities that corresponds to the opening 230 (visible in FIG. 9 with the lid 21 in the open position), the access to which is blocked when the lid 21 is in the closed position. In the example shown in the drawings, the opposite extremity of the main hollow body is closed and forms the bottom 301 of said main hollow body. The height of the object inside the package can of course extend above the main hollow body and thus the connecting part 23, into the interior of the space defined by the lid 21 (which is in the form of a shell in the examples shown in the drawings).

The hinge 22 enables the lid 21 to be pivoted between said closed position in which it closes the main hollow body 3, 23, i.e., in which it prevents access via said opening 230 of the main hollow body to the interior of said main hollow body, and an open position in which access to the interior of the main hollow body via said opening 230 is enabled, which allows an operator to remove the contents of the package 6.

A sealing strip 5 is affixed to the edges of a slot 20 defined between the lid 21 and the connecting part 23, as well as to the hinge 22.

Sealing Strip

The sealing strip 5 binds, on the outer side of the upper shell 2, the edge of the lid 21 and that of the connecting part 23, which are positioned facing each other when the lid 21 is closed (or lowered), over the entire length of the edges of the shells of the package and from one edge to the other, so as to seal the package.

Preferentially, the sealing strip 5 is affixed by one of its extremities to the hinge 22, extended along the edges of the lid 21 and the connecting part 23, which extend face to face with each other, and returns to affix to the hinge 22.

Thus, a very good bacteria and liquid-resistant seal is achieved, with no discontinuity along the opening of the upper shell.

Preferentially, the sealing strip 5 is a peelable strip. When the strip has been affixed, it can be removed by pulling it to peel it off. "Peelable" means that the strip will not tear when it is pulled off, while the adhesive remains on the areas of the previously sealed shells.

According to an example of an embodiment, the sealing strip can be, for example, a thermoadhesive tape made of a synthetic, non-woven, polyethylene fiber material, usually sold under the registered brand name TYVEK.

Protective Cover

A protective cover 1 enables the lid 21 to be covered when said cover is in a position, referred to as the closed position, in which it conceals the sealing strip 5. The cover can be moved, for example raised along axis A1, to a position in which it is separated from the lower shell 3, to enable access to the sealing strip 5.

When the protective cover 1 is in the closed position, the protective cover 1 is close to or in contact with the lower shell 3.

As explained hereafter, the protective cover 1 can be constructed in two parts, 1A and 1B, intended to be assembled one to the other.

Coupling Device

A coupling device 4 is positioned between the protective cover 1 and the lid 21 of the upper shell 2. The coupling device 4 extends into the interior of the cover 1.

The coupling device 4 is designed to keep the protective cover 1 attached to the lid 21 irrespective of the position of the protective cover 1.

When the protective cover 1 is in the open position, the coupling device 4 enables the protective cover to remain attached to the lid. In other words, the cover can be raised with respect to the lid 21 and thus to the lower shell 3, while remaining attached to the lid 21.

When the protective cover 1 is in the open position, the upper extremity of the protective cover 1 is separated from the lid 21, compared to the closed position of the protective cover 1 in which the upper extremity of the protective cover 1 is then in a closer position to the lid 21.

When the protective cover 1 is in the open position, the assembly of the protective cover 1 and the coupling device 4, which remain joined to each other, form a lever arm with regard to the lid 21, which facilitates the opening of the lid 21. This lever arm is attached to the lid 21 by the junction between the coupling device 4 and the lid 21, and the free extremity of this lever arm is formed by the upper extremity of the protective cover 1. Such a lever arm coupled to the lid 21 thus facilitates the opening of the lid 21 by pivoting lid 21 and the lever arm around the axis A22 of the hinge 22.

The coupling device 4 is rigid such that a force applied to the coupling device 4 enables the cover and said coupling device to be pivoted in a direction that is transverse to the axis A1 and to the axis A22 of the hinge 22. "Rigid" means that the structure of the coupling device 4 is adapted in order to transfer to all or part of a force applied to the coupling device 4 (directly or indirectly) to the lid 21 in a direction that is transverse to the axis A1 and to the axis A22 of the hinge 22, or transversally to the mean plane in which the arms of the coupling device extend, for example a direction parallel to the folding axis of each arm, in order to pivot the lid 21 around the axis of the hinge.

In particular, in the examples shown in the drawings, the coupling device is rigid with respect to a force applied to it in a direction that is transverse (or orthogonal) to its median plane in order to cause the lid 21 to pivot around the axis A22 of the hinge 22.

Figure 8:
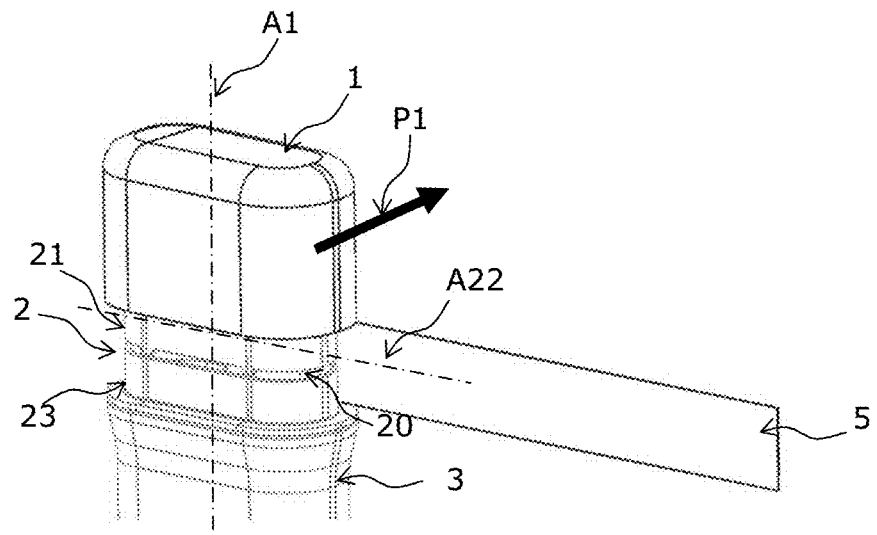
FIG. 8 is a partial perspective view of the package in FIG. 7, shown with the sealing strip removed from the upper shell to which said sealing strip was affixed.
Figure 9:
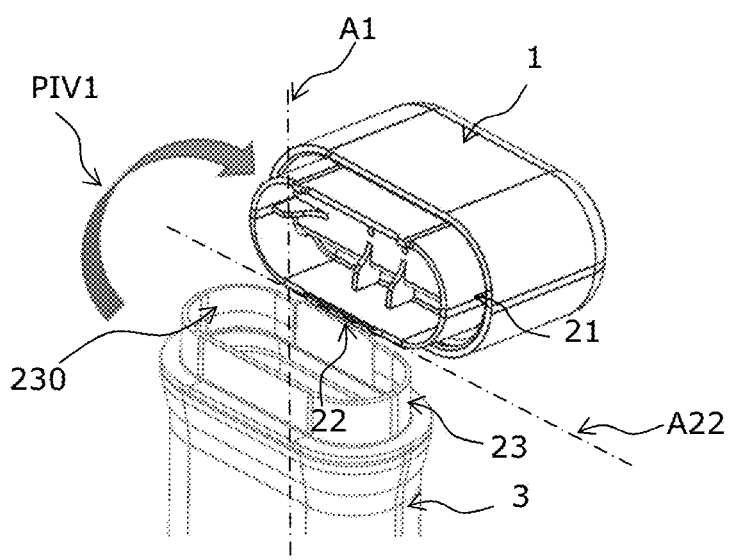
FIG. 9 is a partial perspective view of the package in FIG. 8, shown after having been opened by pivoting the lid of the upper shell.

Indeed, the rigidity of the coupling device 4, in reaction to a force applied to it (via the protective cover 1 on which the operator applies a force P1 as schematized in FIG. 8) that tends to open the lid 21, allows this force to be transferred to the lid 21 and thus to cause the lid to pivot around the axis A22 of the hinge 22.

The coupling device 4 can be devised to be manufactured by means of a plastic injection process in an intermediate position between the deployed position and the folded or contracted position, with, for example, a jointed area along the median plane of the coupling device 4.

When the protective cover 1 is in the closed position (FIG. 6), the coupling device 4 assumes a smaller, contracted configuration in relation to the axis A1, in comparison with its size when the cover 1 is in the open position. In the example shown in particular in FIG. 5, it can thus be seen that the coupling device 4 is folded or contracted.

In said closed position, the protective cover 1 covers the sealing strip 5, thus enabling said sealing strip to be protected.

When the protective cover 1 is in the open position (FIG. 7), the coupling device 4 assumes a larger configuration in relation to the axis A1, in comparison with its size when the cover is in the closed position.

Figure 7:
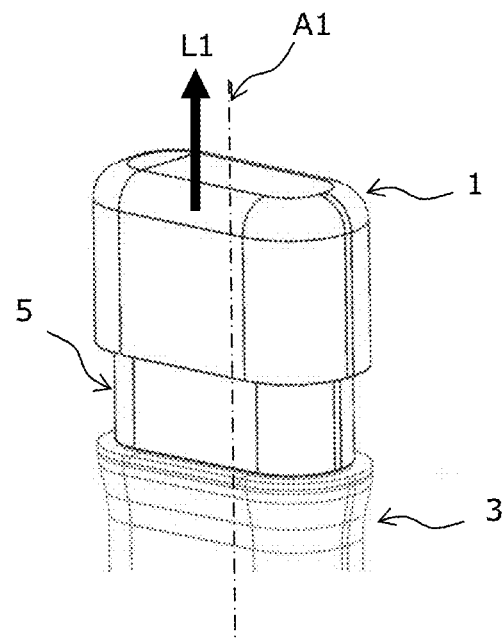
FIG. 7 is a partial perspective view of the package in FIG. 6, shown with the protective cover open such that the sealing strip can be accessed.

In the example shown in particular in FIG. 7 or FIG. 8, the coupling device 4 (not visible due to the protective cover) is deployed. When the protective cover 1 is in the open position (i.e., when the cover is raised in relation to the lower shell), access to the sealing strip is enabled, which allows an operator to remove it.

In the embodiment of FIGS. 16 to 27A, the coupling device 64 is configured to, in the open (raised) position of the cover 61, allow the pivoting of the coupling device 64 by a given angle, preferably of 90°, so as to bring the edge 612 of the opening of the cover 61 into a stable position resting on top of lid 621. The pivoting of the coupling device 64 is done around an axis coincident or parallel to the longitudinal axis A1 of the package. This pivoting mobility is made possible by the coupling system which includes a pin 6432 and a ring 6214, which allows, in the deployed state of the coupling device 64 so that the hooking elements 6413, 6423 are released from the corresponding hooking elements 6217, to let the pin 6432 (which is integral with the coupling device 64) pivot in relation to the ring 6214, which is integral with the lid 621.

This pivoted position of the coupling device 64 and therefore of the cover 61, which remains coupled to the coupling device 64, itself coupled to the lid 621, allows to maintain the cover 61 above the lid 621, and therefore to benefit from a large and stable length of lever arm.

Arm of the Coupling Device

In the example shown in FIGS. 1 to 15, the coupling device 4 comprises two arms 41, 42. The two arms are joined to each other by a lower crossbar 43 and an upper crossbar 44. Preferentially, each crossbar has a reinforcing rib. Preferentially, the coupling device is contracted (folded or compressed) in the initial position.

Figure 2:
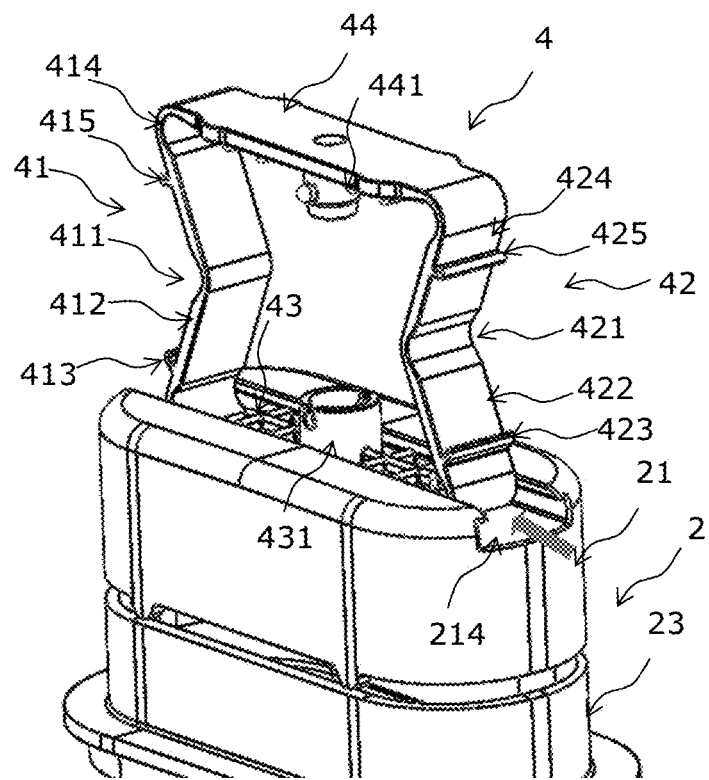
FIG. 2 is a perspective view of a portion of a package according to one embodiment of the invention, showing the coupling of the coupling device to the lid of the upper shell; the cover is not shown and the coupling device is shown in the deployed position to afford a clearer view of the drawing.
Figure 3:
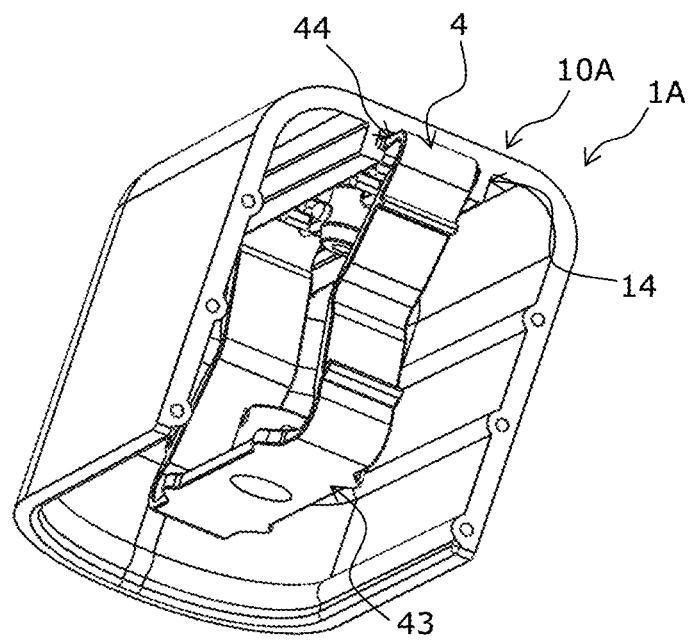
FIG. 3 is a perspective view of a portion of a package according to one embodiment of the invention, showing the coupling of the coupling device to the protective cover; the lid is not shown and the coupling device is shown in the deployed position.
Figure 3A:
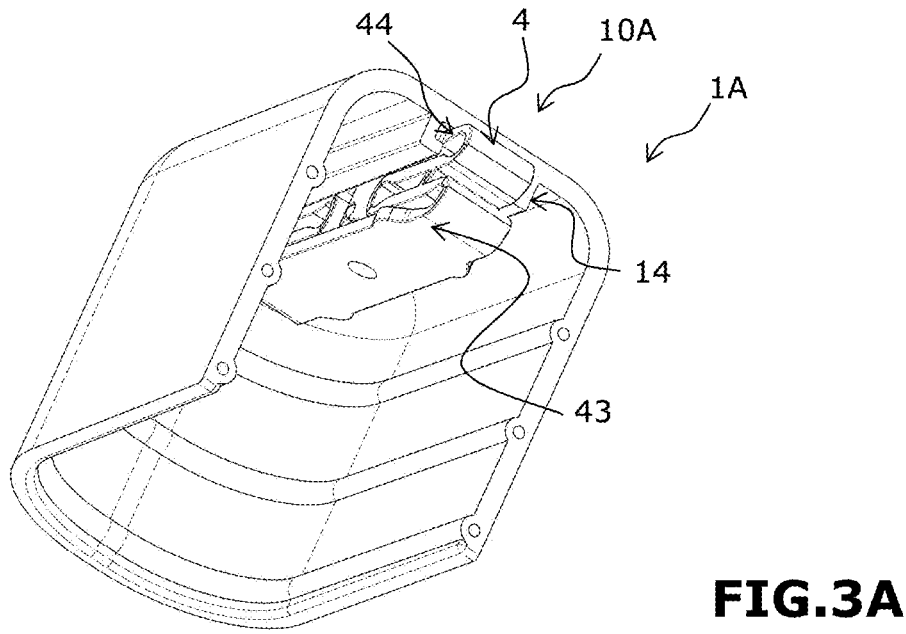
FIG. 3A is a perspective view of a portion of a package according to one embodiment of the invention, showing the coupling of the coupling device to the protective cover; the lid is not shown and the coupling device is shown in the contracted position.
Figure 4:
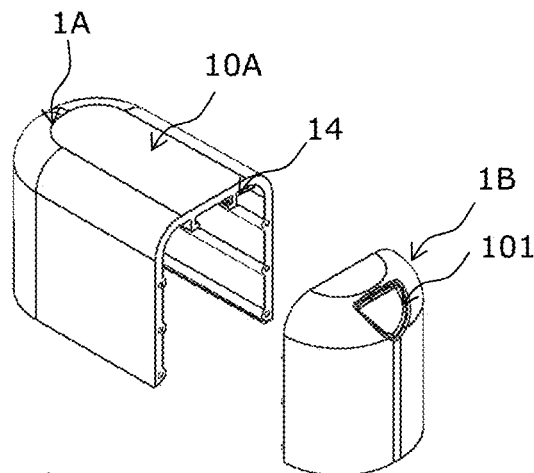
FIG. 4 is a perspective view of a protective cover, constructed of two parts, of a package according to one embodiment of the invention; said parts of the protective cover are shown unassembled.
Figure 5:
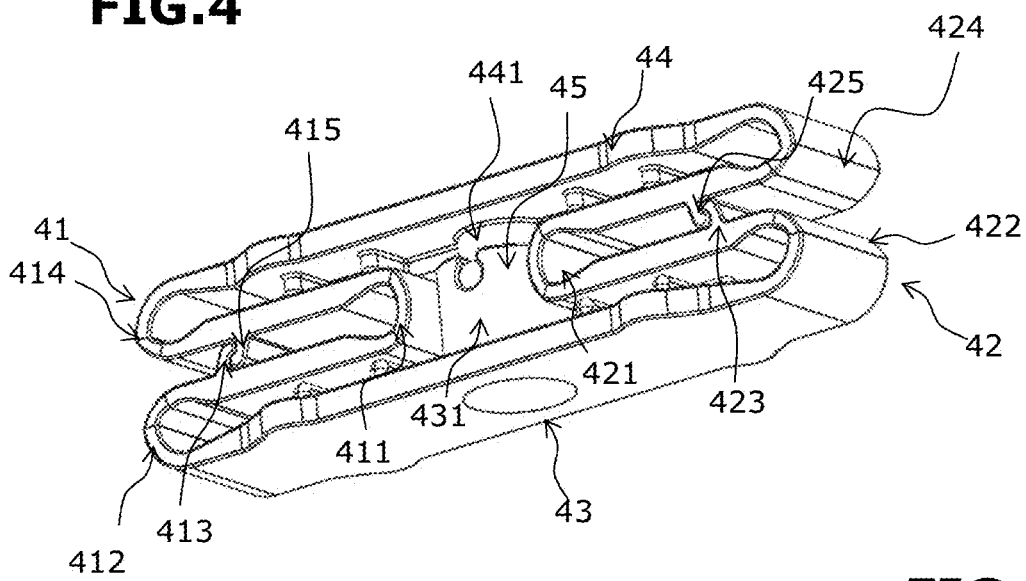
FIG. 5 is a view of a coupling device, for example according to the one in FIG. 2 or 3, of a package according to one embodiment of the invention; said coupling device is shown in the folded position.

In the example shown more particularly in FIGS. 2 and 5, each arm 41, 42 has a bend 411, 421. In other words, each arm 41, 42 is generally V-shaped. According to a particular aspect, the bend is positioned towards the inside of the coupling device 4, i.e., towards the inside of the deformable frame formed by the arms 41, 42 and the crossbars 43, 44 of the coupling device.

The arms 41, 42 can be folded and unfolded at their bends 411, 421. The coupling device 4 is designed to enable symmetrical deformation of both arms 41, 42, enabling movement from an unfolded position to a folded position while keeping the coupling device 4 rigid if a force is applied to the coupling device 4 in a direction that is transverse to the axis A1 and the axis A22 (or in a direction that is transverse to the median plane running between the arms 41, 42).

According to a particular aspect, the material of each arm 41, 42 can be thinner at the bend 411, 421 to form the folding lines facilitating the movement of the coupling device 4 from its folded or contracted position to its unfolded or deployed position, and inversely. As an alternative, the material can also be recessed.

According to an embodiment, and as shown more particularly in FIGS. 2 and 5, each arm 41, respectively 42, has a hooking system 413, 415, respectively 423, 425, designed to hold the two arm 42 portions 422, 424, respectively 412, 414, that extend on either side of the bend 421, respectively 411, against each other when the arm 42, respectively 41, is in the folded position.

In the example shown more particularly in FIGS. 2 and 5, the hooking system thus comprises two hooks 413, 415 for the arm 41 and two hooks 423, 425 for the arm 42, which are able to work together. The hooks are distributed on each side of the bend of the corresponding arm.

The hooks of one arm work together with the hooks of the other arm when the corresponding arm is folded. The hooks can be released from each other by elastic deformation when the coupling device 4 is subjected to an axial force (along axis A1) exceeding a threshold value that causes the corresponding arm to unfold.

Such a hooking system enables the risk of deformation of the crossbars of the coupling device to be limited.

In the embodiment of FIGS. 16 to 27A where the coupling device presents arms 641, 642, the hooking system described above is preferably replaced by hooking elements 6413, 6423 intended to snap into corresponding housings 6217 provided on the lid 621.

The hooking elements 6413, 6423 can be disengaged from the housings 6217 by elastic deformation when the coupling device 64 is subjected to an axial force (along axis A1) exceeding a threshold value that causes the corresponding arm 641, 642 to unfold.

In the example of FIGS. 16 to 27A, the arms 641 and 642 which interconnect the crossbars 643 and 644 are folded towards the outside of the coupling device 64, that is to say, towards the outside of the deformable frame formed by the arms and crossbars of the coupling device.

According to a particular aspect and in a similar manner to that which has been described for the coupling device 4, the arms 641 and 642 of the coupling device 64 also have reductions or recesses of material so as to form folding caps 6411 and 6421 (shown in FIGS. 18 and 18A) facilitating the passage of the coupling device from its folded or contracted position to its unfolded or deployed position, and vice versa.

Fastening System

The coupling device 4 comprises a fastening system 45 that enables the coupling device 4 to be kept in the folded or contracted configuration, corresponding to the closed position of the protective cover 1. The coupling device 4 thus enables the protective cover to be kept in a closed position.

However, the fastening system 45 can be disabled when the protective cover 1 is moved from its closed position to its open position to enable the coupling device 4 to deploy.

In the example shown more particularly in FIGS. 2 and 5, the centering system 45 comprises a pin 441 on one 44 of the crossbars that can work with a corresponding housing (or drum) 431 where the other crossbar 43 is fitted.

Thus, when the closing cover 1 is in the closed position, i.e., when the cover is positioned close to the lower shell, the pin 441 engages by clicking into the housing (or drum) 431, such that the crossbars 43 and 44 are kept positioned close to each other.

The male 441 and female 431 parts of the fastening system for the crossbars 43 and 44 can be released from each other by elastic deformation (unlatching), when the coupling device 4 is subjected to an axial force (corresponding to the force applied to move the protective cover to the open position) exceeding a threshold value that causes the crossbars 43, 44 to spread apart from each other.

According to a particular aspect, the coupling device is kept centered with respect to the lid 21 and/or the cover 1. In the example shown in the drawings, the fastening system 45 enables the coupling device 4 to thus be centered with respect to the cover and/or the lid 21. Thus, according to a particular aspect, the pin 441 and the housing 431 are centered on the crossbars. As a result, when the fastening system 45 is activated, the crossbars 44 and 43 are centered on each other.

In particular, when the protective cover 1, which remains joined to the lid 21 by the coupling device 4, is in the open position, the protective cover 1 pulls on the upper crossbar 44 of the coupling device 4, which releases the two parts 431, 441 of the fastening system 45 from each other. When the protective cover 1 is moved, it remains joined to the upper crossbar 44 of the coupling device 4, and the lower crossbar 43 of the coupling device 4 remains joined to the lid 21.

According to some embodiments and as can be seen in the example shown in FIGS. 2 and 5, the coupling device 4 remains in a folded or contracted position having substantially the same symmetrical axis as the one it has when unfolded or deployed.

An inverted distribution of the male element (pin) and the female element (housing) can be expected on the crossbars. Thus, in the example shown in FIGS. 16 to 27A, the coupling device 64 is equipped with a fastening system 645 which comprises a pin 6431 which is provided with one 643 of the crossbars (the one intended to be coupled to the lid 621) which is able to work with a corresponding housing (or drum) 6441 with which the other crossbar 644 is provided (the one intended to be coupled to the cover).

Assembling the Coupling Device

According to a particular aspect shown in FIGS. 1 and 2, the lid 21 has an insert housing 214, which is preferably incorporated at the level of the lid 21. The insert housing 214 is built into the outer side of the upper wall.

In the example shown, the housing 214 is formed by a slot whose section delineates a generally T-shaped or dovetail-shaped passage.

Advantageously, the slot has an opening at one extremity at least to enable the lateral insertion of the crossbar 43 of the coupling device 4 into the slot (see FIG. 2), by relative movement between the coupling device 4 and the lid 21.

As an alternative, the insert housing 214 can be formed by an indent, equipped with holding clips, designed to receive and hold the crossbar 43 of the coupling device 4 with respect to the lid 21.

The cover 1 also has an insert housing 14 designed to receive the upper crossbar 44 of the coupling device 4. The insert housing 14 is built into the inner side of the upper part of the cover 1.

In particular, the cover 1 comprises two parts 1A, 1B that can be assembled to enable the coupling device 4 (in particular the crossbar 44) to be mounted to the insert housing 14 by a lateral opening in the part 1A that is equipped with said insert housing 14. The part 1B enables the lateral opening of the part 1A of the protective cover 1 to be closed.

Figure 22:
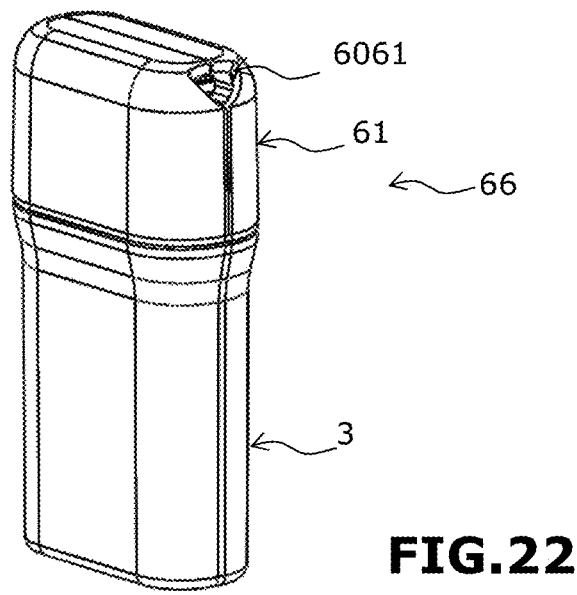
FIGS. 22, 23, 24, 25, 26, 27, and 27A illustrate the opening steps of a package consistent with that of FIG. 16.

The part 1B has an orifice 101 to make it easy to grasp a heat-shrink plastic wrap that can be wrapped around the package to protect it from dust, or to enable the exchange of gas during sterilization with gas, such as ethylene oxide. In the embodiment of FIG. 22, the cover 61 also includes a similar orifice referenced 6061.

As an alternative, the insert housing 14 can be formed by an indent, equipped with holding clips, designed to receive and hold the crossbar 44 of the coupling device 4 with respect to the protective cover 1.

As an alternative, the coupling device 4 can be devised to be formed in one piece with the lid 21 or the protective cover 1.

The coupling device 4 is attached to the part 1A of the protective cover 1 by relative movement of the one with respect to the other. Preferentially, the coupling device 4 is assembled to the lid 21 prior to affixing the sealing strip 5 onto the slot 20.

In particular, it can be devised to assemble the coupling device 4 to the lid 21, affix the sealing strip 5 to the lid 21, then to assemble the part 1A of the protective cover 1 to the coupling device 4, and lastly to close the part 1A of the protective cover 1 with the part 1B of the protective cover.

As an alternative, the coupling device 4 can be assembled to the lid 21 after the sealing strip 5 has been affixed to the slot 20.

Figure 17:
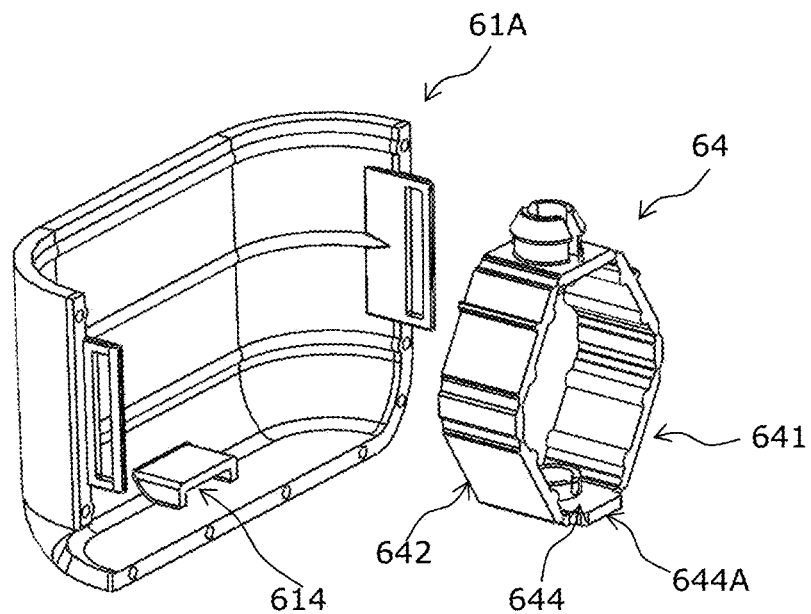
FIG. 17 is a pre-assembly view of part of the cover of the package of FIG. 16 with the coupling device.
Figure 17A:
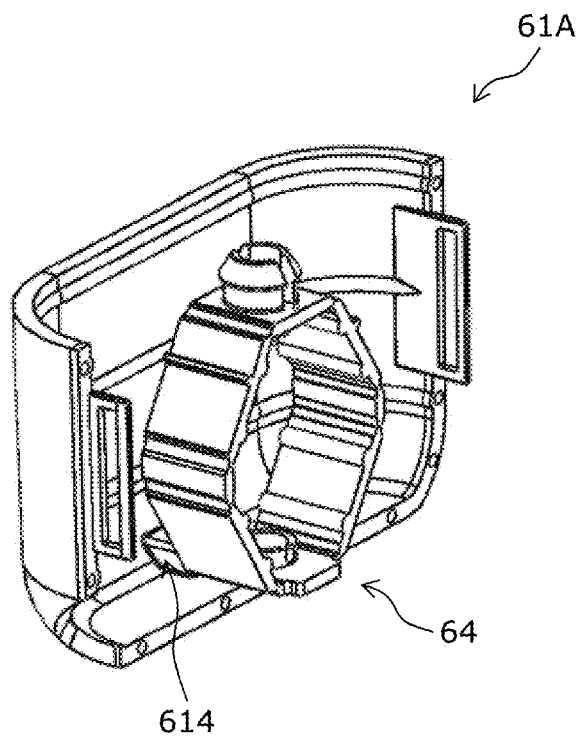
FIG. 17A is an assembled view of the part of the cover and the coupling device in FIG. 17.

In the embodiment of FIGS. 16 to 27A, the specific system for receiving the coupling device 64 in the cover 61 comprises receiving housings 614 arranged in the two parts 61A, 61B of the cover (see FIGS. 17 and 17A). These housings 614 can each receive a fin 644A (also called assembly fin) of the coupling device 64. In the example of FIG. 16, each fin is formed by an end portion of the crossbar 644 of the coupling device 64.

In the example of FIG. 16, the protective cover 61 is realized in two parts, preferably substantially symmetrical, with a median assembly plane which extends along the length of the cover 61 and perpendicular to the opening plane of this cover.

As mentioned above, the coupling device 64 comprises assembly fins which are arranged orthogonally to the assembly plane of the two parts of the cover 61, in the assembled state of the coupling device with said parts of the cover 61. These assembly fins are arranged along an axis which is parallel to the folding/unfolding axes of the arms 641, 642 of the coupling device 64. The coupling device 4 has a median plane in which the two arms 641, 642 extend. The assembly fins are arranged on either side of this median plane.

According to one embodiment, the coupling device moves from the contracted position to the deployed position by plastic deformation in order to avoid or limit any spring-back effect in the contracted position.

In the examples shown in the drawings, the coupling device is shown as a body with a deformable closed contour. In the unfolded or deployed position, the closed contour defines a through passage.

Figure 18:
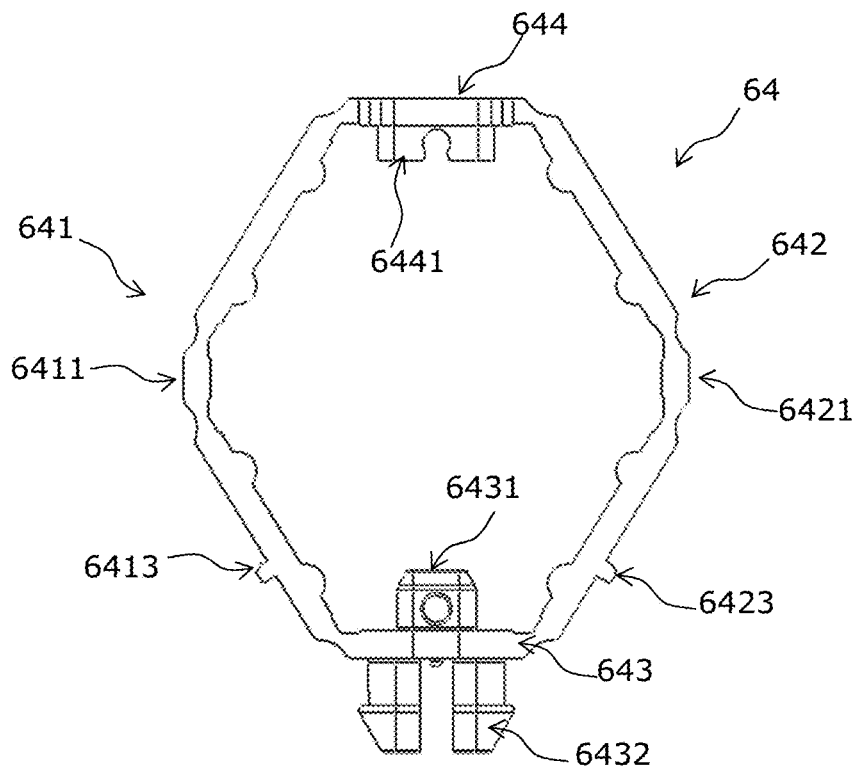
FIG. 18 is a front-facing view of the coupling device of the package of FIG. 16 in the deployed position.
Figure 18A:
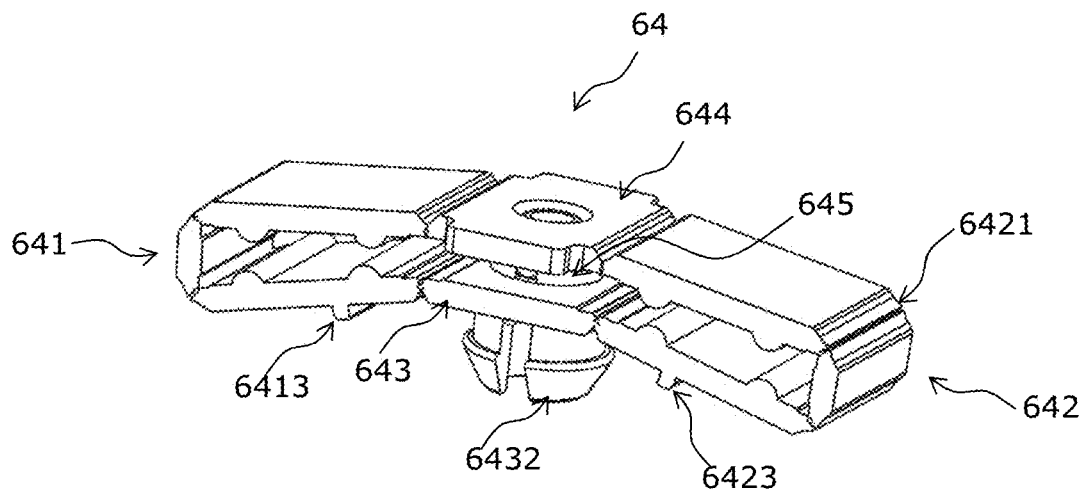
FIG. 18A is a perspective view of the coupling device of FIG. 18 in a folded (retracted) position.
Figure 19:
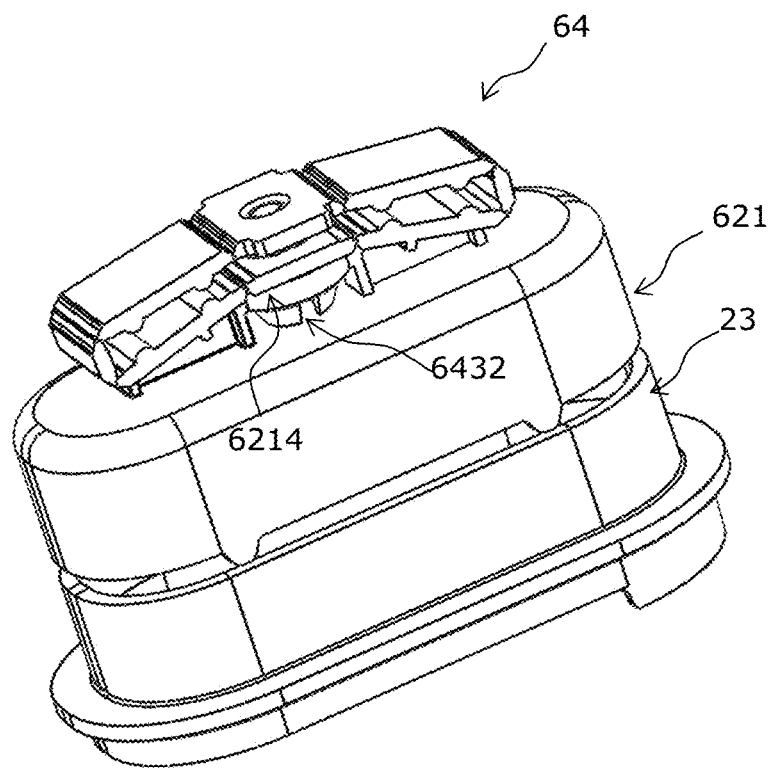
FIG. 19 is a perspective view of the coupling device of the package of FIG. 16 in a folded position and coupled with the lid.

In the embodiment of FIGS. 16 to 27A, the coupling device 64 is coupled to the lid 621 by a coupling system, preferably by snap-fastening, of a male element, such as a pin 6432, preferably formed on the crossbar 643 on the outside, in a female element, such as a housing, for example, formed by a ring 6214, preferably formed on the lid 621. In the example of FIG. 18, the pin 6432 is split axially and has a frustoconical end, adapted for insertion with retention in the ring 6214.

The coupling system 6432/6214, once activated, opposes the withdrawal of the coupling device 64 in relation to the lid 621 by traction, but allows, in the deployed state of the coupling device 64, a pivoting of the coupling device 64 in relation to the lid 621 around an axis coincident or parallel to the axis A1, preferably according to a given angular range.

Figure 20:
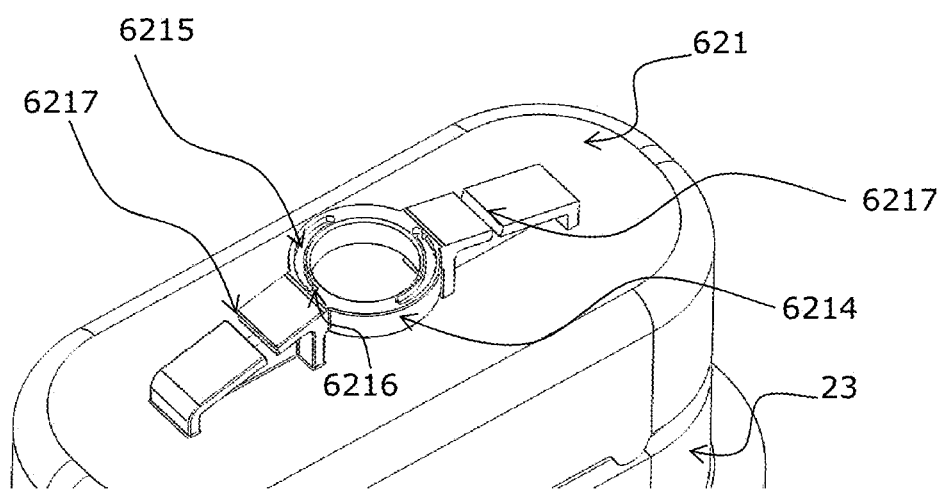
FIG. 20 is a partial view from above the lid showing a coupling system on the lid of the package in FIG. 16 and intended to work with a corresponding system provided on the coupling device.
Figure 21:
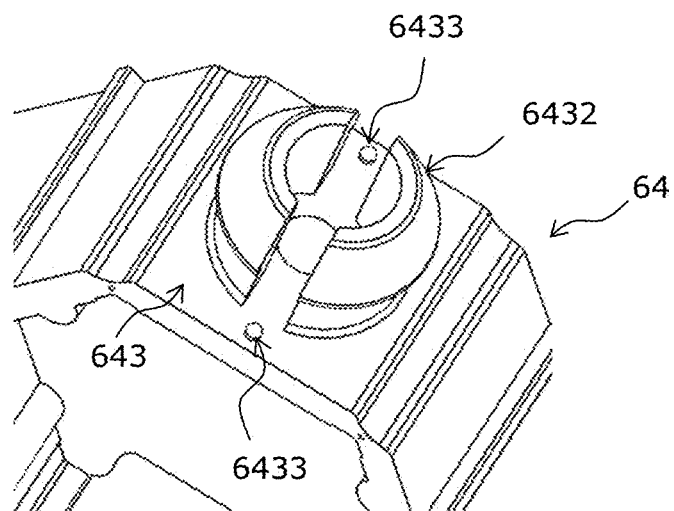
FIG. 21 is a partial view of the coupling device showing a coupling system on the coupling device of the package of FIG. 16 and intended to work with a corresponding system provided on the lid.

In the example of FIG. 20, the ring 6214 is comprised, on its upper face, of rails 6215 formed by curved grooves which can receive lugs 6433 associated with the pin 6432 and formed on the coupling device 64. The rails 6215 allow to guide a pivoting movement of the coupling device 64 in relation to the lid 621 by working with the lugs 6433 of the coupling device 64 in the rails 6215 of the female element of the lid 621.

Fastening means are provided to hold the coupling device 64 in a rotated position by a given angle in relation to the lid 621, preferably an angle of 90°. In particular, in the example illustrated in FIG. 20, each rail comprises at one end, a system for holding the lug, for example, formed by a housing 6216 having a local narrowing of the rail before the end, so that, once this narrowing has passed, the lug 6433 is held at this end of the rail 6215.

According to a particular aspect, each arm 641, 642 has a hooking element 6413, 6423 configured, in the folded position of the coupling device 64, to work with a complementary hooking element 6217, such as a slot made in an element counter-form present on the lid 621. These hooking elements 6413, 6423, 6217 hold the corresponding arm against the lid.

In the closed configuration of the cover 61, the cover 61 mainly covers, preferably completely, the lid 621, and the coupling device 64 is in the folded configuration.

When the operator pulls on the cover 61 along the axis A1, the cover 61 is brought into the raised configuration in relation to the lid 621 by setting the coupling device 64 in the deployed position. In this simply lifted configuration of the cover 61 (not yet pivoted), in projection along the axis A1 and in an orthogonal plane in relation to the axis A1, the outside outline of the lid 621 remains inside the outside outline of the cover 61.

In the raised and pivoted configuration of a given angle, for example 90°, of the cover 61 in relation to the lid 421 around the axis A1, the edge 612 of the opening (lower periphery) of the cover 61 is positioned by resting on the lid 621, which keeps the cover 61 in the raised position in relation to the lid 621 by preventing the cover 61 from going down.

In this raised and pivoted configuration of the cover 61, in projection along the axis A1 and in an orthogonal plane in relation to the axis A1, the outer outline of the lid 621 extends partly outside the outer outline of the cover 61.

This pivoted raised configuration of the cover 61 (which also drives the connection device in the deployed and pivoted configuration), thus allows to maintain free access for the user to the upper shell 62, and in particular to the sealing strip 5. Then the sealing strip can be easily removed. The pivoting of the cover 61 above the lid 621 allows to obtain a maximum and stable height of the cover 61, which allows to form an effective lever arm for opening the lid 621 by pivoting the assembly of the cover 61 and the lid 621 relative to the connecting part 23 of the upper shell 62 around the axis A22 of the corresponding hinge 22.

Unpackaging Process

FIGS. 6 to 11 illustrate various stages in an opening sequence of the package 6.

Figure 6:
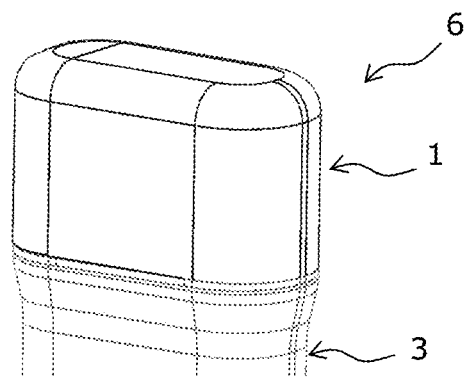
FIG. 6 is a partial perspective view of a package according to one embodiment of the invention, shown with the protective cover closed.

Initially, and as shown in FIG. 6, the protective cover 1 is in the closed position. The protective cover 1 is close to the lower shell 3 and covers the sealing strip 5.

The operator pulls with a corresponding force L1 (FIG. 7) on the protective cover 1 such that the protective cover 1 lifts with respect to the lower shell 3. The protective cover 1 is thus in the open position. The force L1 is applied along the axis A1 (longitudinal axis of the package).

The force L1 enables the fastening system 45 (FIG. 5) to be disabled by pulling on the crossbar 44 of the coupling device 4 that is attached to the inside of the protective cover 1, which releases the male 441 and female 431 parts from each other. The fastening system for the arms 41, 42 is also disabled by this force L1 such that the coupling device 4 accompanies the movement of the cover 1 by unfolding its arms 41, 42. Preferentially, the coupling device 4 undergoes a plastic deformation, in particular of its arms, when the system initially formed by the folded arms assumes the deployed position.

The sealing strip 5 is thus uncovered and can be pulled off as shown in FIG. 8. The hinge 22 that joins the lid 21 to the connecting part 23 (and thus to the lower shell 3) is then no longer restrained by the sealing strip.

The operator can thus apply a force P1, schematized in FIG. 8, to the protective cover 1 to cause the lid 21 to pivot around the axis A22 of the hinge 22. In particular, this force P1 is a force that is transverse to the axis A1 of the package and the axis A22 of the hinge, which is transferred by the protective cover 1 to the lid 21 by the coupling device 4 whose structure makes it rigid with respect to such a force. It can also be seen that the force P1 is transverse to the median plane running through the arms of the coupling device.

The coupling device 4 and the protective cover 1 thus form, when in the open position, a lever arm on the lid 21. The force P1 applied to this lever arm causes the pivoting PIV1 of the lid 21, which is schematized in FIG. 9.

Figure 10:
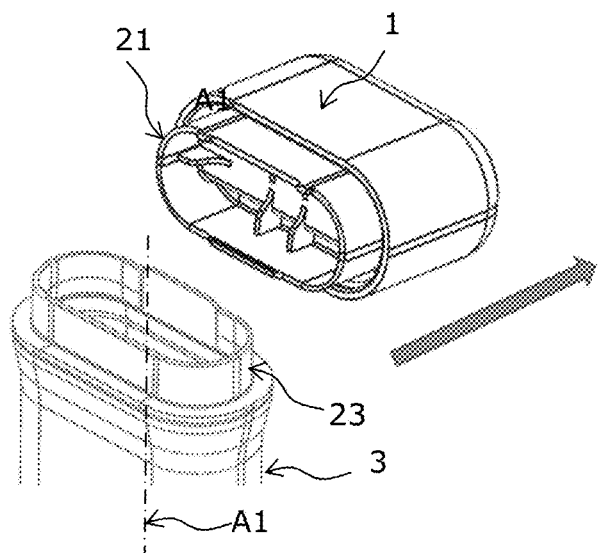
FIG. 10 is a partial perspective view of the package in FIG. 9, shown with the hinge broken off by pulling.
Figure 11:
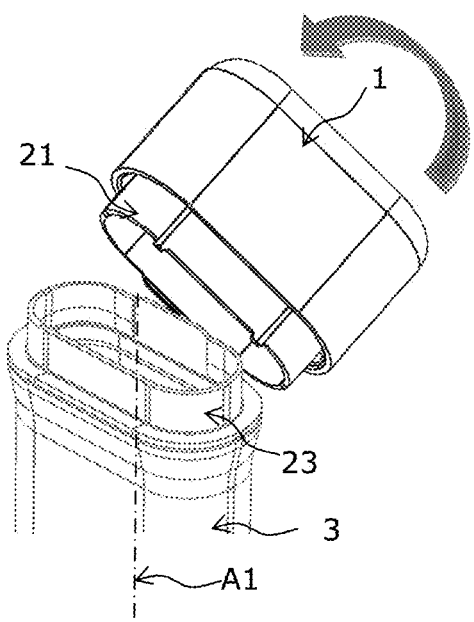
FIG. 11 is a partial perspective view of the package in FIG. 10, shown with the hinge broken off by twisting.

The operator can, as shown in FIG. 10, remove the lid 21, which is pivoted to the open position, from the connecting part 23, by pulling on the lid or the cover until the hinge breaks. As an alternative, as shown in FIG. 11, the operator can separate the lid 21, which is pivoted to the open position, from the connecting part 23, by means of a twisting movement by turning the lid or the cover around an axis that is transverse to the hinge until the hinge breaks.

The operator can then remove the object contained in the remaining main hollow body, which corresponds to the lower shell 3 and to the connecting part 23. It can also be devised that the operator remove the object contained therein without breaking the hinge 22.

As recalled above, the contents removed can be another package (inner package) and/or a gripper coupled to an object (also referred to as a system for holding an object) or even the object itself.

FIGS. 22 to 27A describe various stages in an opening sequence of the package 66. The steps described above for the package 6 are applicable to the package 66 with in addition a step of pivoting the cover 61 to maintain it in the raised position above and resting on the lid 621.

Initially, as shown in FIG. 22, the cover 61 of the package 66 is in the closed position, the coupling device 64 being in the folded (retracted) configuration. The fastening system 645 is active and the arms 641, 642 are kept coupled to the lid 621 by working with the hooking elements 6413, 6423 with the corresponding elements 6217.

Figure 23:
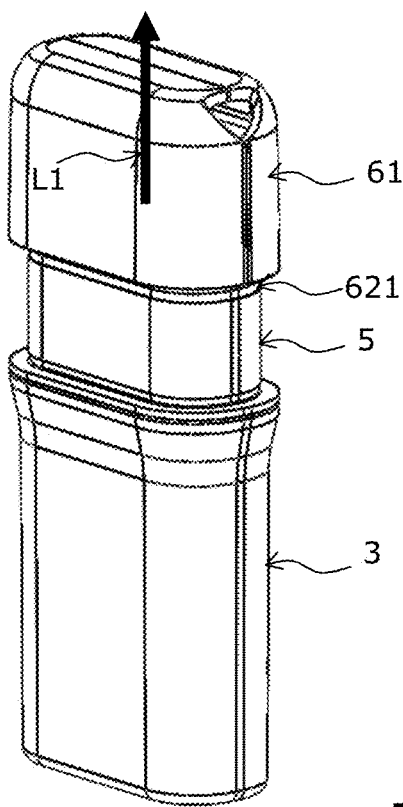

As illustrated in FIG. 23, to open the package 66, the user pulls on the cover 61 to move it away from the lower shell 3, and thus uncover the sealing strip 5. The user thus exerts a force on the cover 61 in a direction L1 parallel to the axis A1. The displacement of the cover 61 causes the deployment of the coupling device 64 by deactivating the fastening system 645 and the coupling between them of the hooking elements 6413, 6423, 6217.

Figure 24:
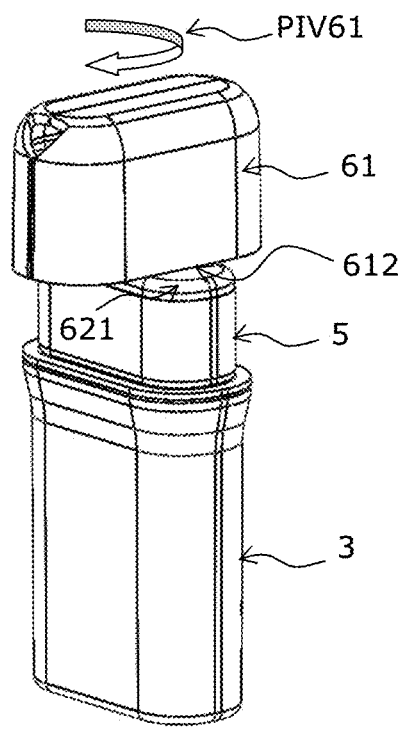

Preferably, and as illustrated in FIG. 24, the user pivots (arrow PIV61) the cover 61 around an axis parallel or coincident with the axis A1, thanks to the pivoting coupling offered by the coupling system (pin 6432/ring 6214) between the coupling device 64 and the lid 621. The user can thus guide the cover 61 transversely, preferably orthogonally, to the lid 621 to bring the edge of the opening of the cover 61 to rest on the top of the lid 621 and to thus maintain the distance between the cover 61 and the lower shell 3, which not only allows easy access to the sealing strip 5 without the cover 61 falling, but also to obtain a large lever arm formed by the cover 61, connected to the lid 621 by the coupling device 64, which is spaced from the axis A22 of the hinge, and whose position is stable thanks to its pivoted position resting on the lid 621. The user can thus easily open the lid 621 with respect to the connecting part 23 by using the cover 61 as a lever arm.

According to a particular aspect, the angle of the pivoted position of the cover 61 is maintained by engagement of the lugs 6433 of the coupling device 64 in the fastening housings 6216 formed at one end of each of the rails 6215 of the ring 6214.

Figure 25:
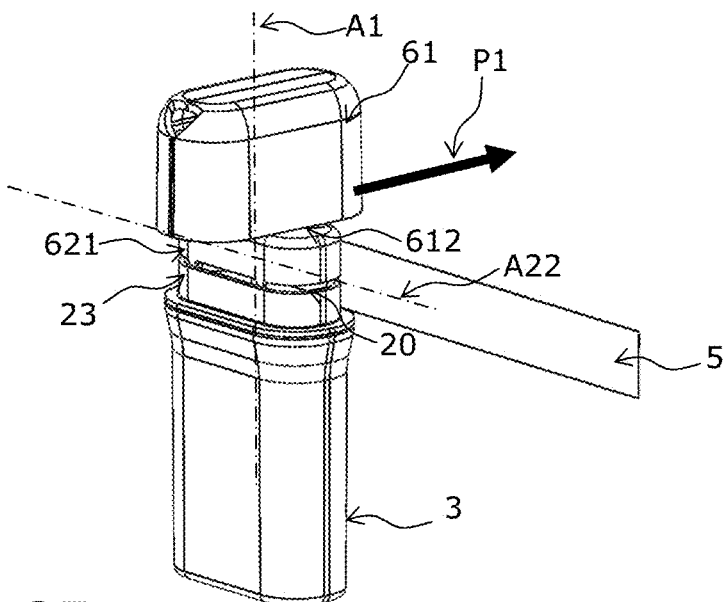
Figure 26:
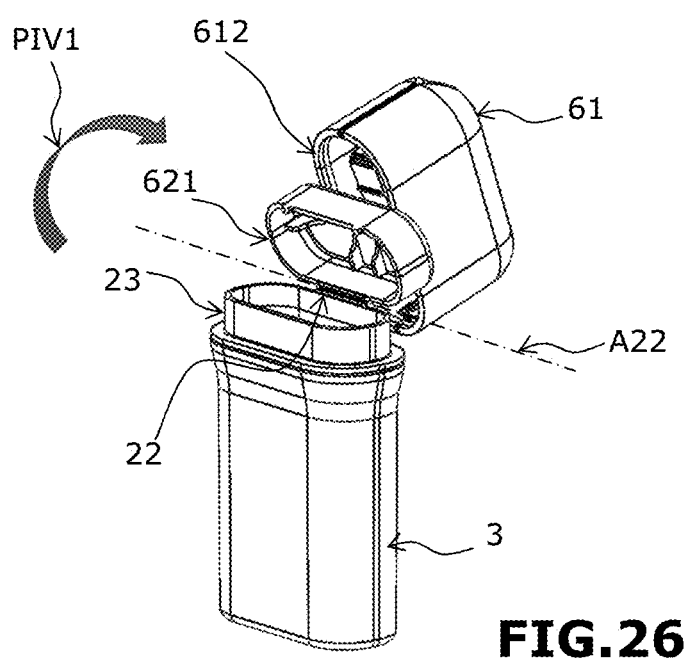

As illustrated in FIGS. 25 and 26, the user removes the sealing strip 5, then pulls on the cover 61 in transversally to the axis A1 and to the axis A22 of the hinge, for example in the direction P1, to pivot the assembly of the cover 61 and the lid 621 in order to open the lid 621 in relation to the hollow body 3, 23. The coupling system 6432, 6214 between the coupling device 64 and the lid 621 allows to transmit to the lid 621 the force applied to the cover 61 (passing through the coupling device 64).

Figure 27:
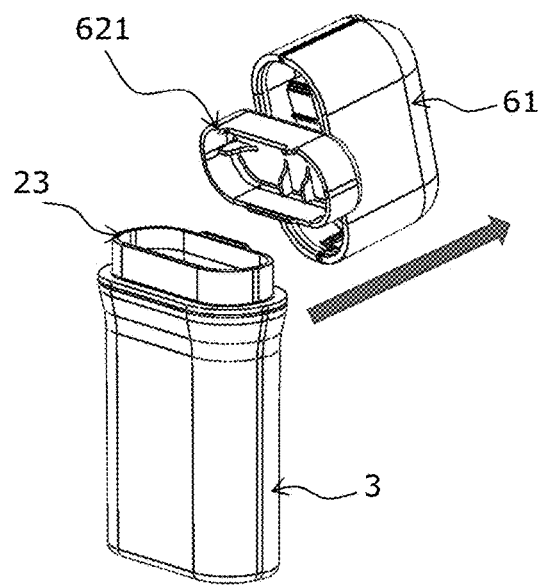
Figure 27A:
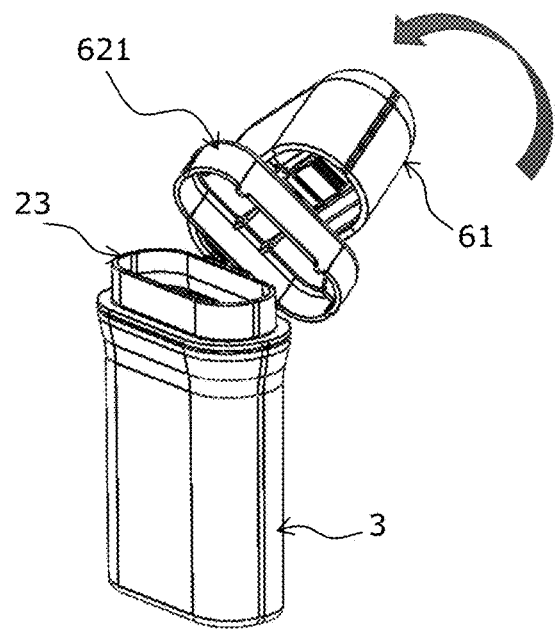

The operator can, as shown in FIG. 27, remove the lid 621, which is pivoted to the open position, from the connecting part 23, by pulling on the lid or the cover until the hinge breaks. As an alternative, as shown in FIG. 27A, the operator can separate the lid 621, which is pivoted to the open position, from the connecting part 23, by means of a twisting movement by turning the lid 621 or the cover 61 around an axis that is transverse to the hinge until the hinge breaks.

Thanks to the coupling device between the protective cover and the lid, when the protective cover is moved to the open (raised) position, being preferably further pivoted relative to the lid for the embodiment of FIGS. 16 to 27A, the protective cover remains linked to the lid by the coupling device, while the coupling device and the protective cover form a lever arm associated with the lid, the length of which has increased in relation to the closed position of the cover, which facilitates the opening of the lid with a retracted effort on the cover.

This lever arm enables the operator, when the fastening system, if any, has been removed, undone or broken, to easily pivot the lid around the hinge by applying force to the extremity of this lever arm formed by the protective cover.

After the lid has been opened, and preferably removed, the contents (inner package or object) can be removed from the package.

The separation of the cover with regard to the hollow body, when the cover is in the open position, not only enables the formation with the coupling device of said lever arm joined to the lid, but also, after the lid has been pivoted open, the access to the interior of the hollow body.

It can indeed be devised that, after opening, the lid and cover assembly be pivoted around the axis of the hinge, for example at 180°, such that the operator's fingers holding the hollow body and the package are kept away from the opening of the hollow body.

The removal of the lid, to which the cover remains joined, enables the cover to be separated from the remainder of the hollow body accommodating the contents, to avoid the risk of unintentional contact with said cover, which could lead to a loss of asepsis, when the contents (inner package or object) are grasped and/or when they are removed from the package.

The area of access to the interior of the container can thus be correctly cleared, which enables the operator to grasp the contents without risking any loss of asepsis.

Due to the lever arm formed by the assembly formed by the protective cover and the coupling device when the protective cover is in the open position, the force to be applied on the protective cover in order to pivot the lid is less than that which would have to be applied directly to the lid if there were no coupling device and protective cover on the lid.

According to a particular aspect, opening the cover completely (for example by pivoting it 180° around the axis of the hinge or by separating it from the hollow body) enables the cover to be separated from the access area corresponding to the space above the opening of the hollow body (i.e., the content removal space), which limits the risk of loss of asepsis when the object, which can be in an inner package, is grasped. Loss of asepsis may indeed result from the immediate proximity of a residual portion of the cover near the fingers of the sterile operator (for example, the sterile nurse or the surgeon).

Alternative Coupling Devices

Figure 13:
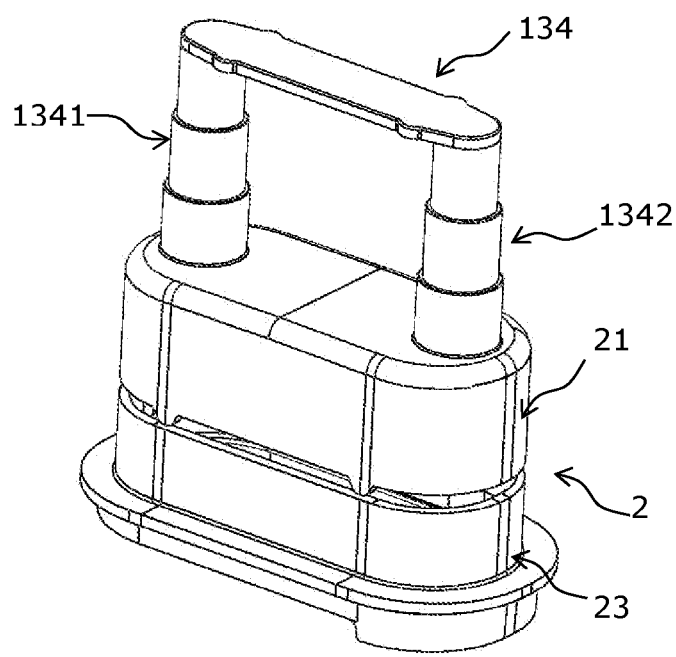
FIG. 13 is a perspective view of a lid and a coupling device (without the cover) of a package according to another alternative embodiment of the invention, in which the coupling device is telescopic.

According to an alternative embodiment shown in FIG. 13, the coupling device is referenced 134 and has two telescopic arms 1341, 1342.

The ability to vary the height of the arms along the axis A1 thus results from the capacity to extend the parts of each telescopic arm in relation to each other, whereas in the alternative with the bend (FIGS. 1 to 9), the variable height results from the folding/unfolding capacities of the arms at the level of the bends.

In the example shown in FIGS. 1 to 9, presented above, the crossbars of the coupling device are elements of the coupling device that are separate from the protective cover and the lid. As an alternative, it can be devised that these crossbars be formed by parts of the protective cover 1 and/or the lid 21. It can in particular be devised that the arms of the coupling device be directly attached to the protective cover 1 and to the lid 21.

Figure 12:
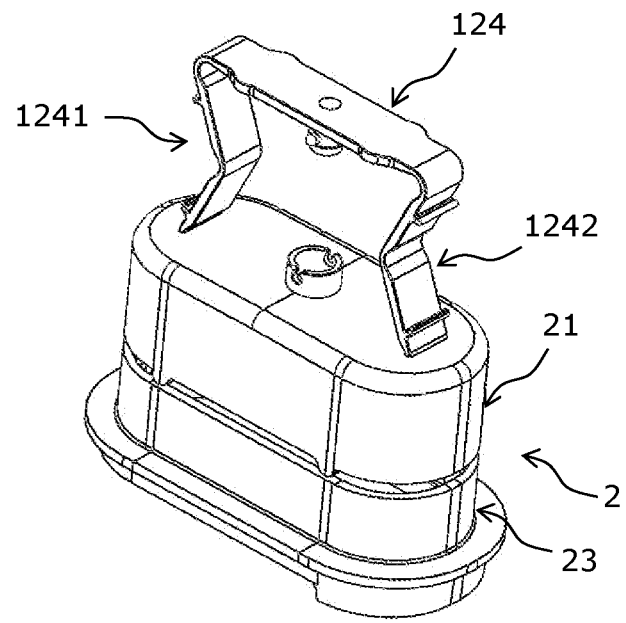
FIG. 12 is a perspective view of a lid and a coupling device (without the cover) of a package according to an alternative embodiment of the invention.

Thus, in the example shown in FIG. 12, the coupling device (referenced 124) comprises a portion forming an upper crossbar and it can be considered that the lower crossbar is formed by the upper portion of the lid 21 to which the arms (referenced 1241, 1242) of the coupling device are joined.

In the example shown more particularly in FIGS. 2 and 5, the coupling device 4 and the lid 21 are separate parts. According to different embodiments, the coupling device 4 and the lid 21 can be formed in one piece.

Similarly, in the example shown in FIG. 13, it can be considered that the lower crossbar is formed by the upper portion of the lid 21 to which the arms (referenced 1341, 1342) of the coupling device are joined.

The invention is not limited to the embodiments shown in the drawings. Consequently, it must be understood that, when the characteristics referred to in the appended claims are followed by reference numbers, these numbers are included solely to improve the readability of the claims and are in no way limiting with regard to the scope of the claims.

In addition, the term "comprising" does not exclude other elements or steps. Moreover, the characteristics or steps that have been described with reference to one of the embodiments described above can also be used in combination with other characteristics or steps in other embodiments described above.

The invention claimed is:

1. A package (6; 66) designed to contain an object, said package comprising:
   a hollow body (3, 23) with an opening (230) through which said object passes into and out of said hollow body (3, 23);
   a lid (21; 621) joined to the hollow body (3, 23) by a hinge (22), enabling the hollow body (3, 23) to be closed;
   a protective cover (1; 61); and
   a coupling device (4; 64) between the protective cover (1; 61) and the lid (21; 621), said protective cover (1; 61) being movable between:
      a closed position in which the protective cover (1; 61) covers the lid (21; 621) and in which the coupling device (4; 64) assumes a contracted configuration; and
      an open position in which the protective cover (1; 61) is spaced from the hollow body (2, 23) and in which the coupling device (4; 64) assumes a deployed configuration, wherein the protective cover (1; 61) forms with the coupling device (4; 64), in said open position, a lever arm coupled to the lid (21; 621).

2. A package (6; 66) according to claim 1, in which said package (6; 66) comprises a closure system (5) configured to be removed, undone or broken, thereby enabling the lid (21; 621) to be kept in the position which it closes the hollow body (3, 23).

3. A package (6; 66) according to claim 1, in which said package (6; 66) comprises a sealing strip (5) that is affixed to the edges of a slot (20) defined between the lid (21; 621) and the first hollow body (3, 23).

4. A package (6; 66) according to claim 1, wherein the hinge (22) comprises an axis (A22) and the hollow body (3, 23) comprises an axis (A1) by which said object is removed through said opening, the coupling device (4; 64) is rigid with respect to a force (P1) applied in direction that is transverse to the axis (A1) of the opening of the hollow body (3, 23) and transverse to the axis (A22) of the hinge (22), to enable the lid (21; 621) to pivot.

5. A package (6; 66) according to claim 1, in which the coupling device (4; 64 comprises a fastening system (45; 645) designed to hold the coupling device (4; 64) in a retracted configuration, folded or contracted, when the protective cover (1; 61) is in the closed position, while enabling said fastening system (45; 645) to be disabled when the protective cover (1; 61) is moved from said closed position to said open position, which causes the coupling device (4; 64) to assume the deployed configuration.

6. A package (6; 66) according to claim 5, in which the coupling device (4; 64) comprises two arms (41, 42; 641, 642), with each arm (41, 42; 641, 642) having a bend (411, 421; 6411, 6421).

7. A package (6; 66) according to claim 6, in which, as the two arms (41, 42; 641, 642) are connected by a lower crossbar (43; 643) and an upper crossbar (44; 643), the fastening system (45; 645) has a male part (441; 6431) attached to one (44; 643) of the crossbars and a female part (431; 6441) to the other crossbar (43; 644), said male and female parts being designed to work together by clicking into each other when the protective cover (1; 61) is in the closed position.

8. A package (6; 66) according to claim 1, in which the coupling device (4; 64) is in the form of a body with a closed contour that can be deformed by pulling.

9. A package (6; 66) according to claim 1, in which the coupling device (4; 64) comprises two arms (41, 42; 641, 642), with each arm (41, 42; 641, 642) having a bend (411, 421; 6411, 6421).

10. A package (6; 66) according to claim 9, in which each arm (41, 42; 641, 642) has thinner material at the bend (411, 421; 6411, 6421).

11. A package (6) according to claim 9, in which each arm (41, 42) has a hooking system (413, 415, 423, 425) designed to hold the two parts (412, 414, 422, 424) of the arms (41, 42) that extend on either side of the bend (411, 421) together when the arm (42) is in the folded position.

12. A package (66) according to claim 9, in which each arm (641, 642) has a hooking device (6413, 6423) designed, with a corresponding hooking device (6217) provided on the lid (621), to maintain the said arm coupled to the lid (621) in a retracted configuration of the coupling device (64).

13. A package (6; 66) according to claim 1, in which the lid (21: 621) has an insert housing (214; 6214) designed to receive and hold a part (43; 6432) of the coupling device (4; 64) with regard to the lid (21; 621).

14. A package (66) according to claim 1, in which said package (66) includes a coupling system (6432; 6214) of the coupling device (64) to the lid (621), the coupling system being designed so that, in the deployed state of the coupling system (64), the coupling system (64) can be pivoted from the lid (621) so that the edge (612) of the opening of the cover (61) can rest on the lid (621).

15. A package (6; 66) according to claim 1, in which the protective cover (1; 61) comprises two cover parts (1A, 1B; 61A, 61B) that are assembled to enable a part (44; 644) of the coupling device (4; 64) to be mounted to the insert housing (14; 614) of one (1A; 61A) of the cover parts (1A, 1B; 61A, 61B) by a lateral opening in said cover part (1A; 61A), and to close said lateral opening by means of the other cover part (1B; 61B).

16. A package (6; 66) according to claim 1, in which an inner package containing an object is accommodated.

17. A package (6; 66) according to claim 1, in which a gripping device coupled to said object is accommodated.

18. A process for unpacking an object accommodated in a package (6; 66) according to claim 1, in which said process comprises the following steps:
- moving the protective cover (1; 61) to the open position, with the protective cover (1; 61) remaining joined to the lid (21; 621) by the coupling device (4; 64); and
- applying a force (P1) on the protective cover (1; 61) to cause the lid (21; 621) to pivot (PIV1) around the axis (A22) of the hinge (22).

19. A process according to claim 18, in which the package (66) comprises a coupling system (6432; 6214) of the coupling device (64) to the lid (621), the coupling system being designed so that, in the deployed state of the coupling system (64), the coupling system (64) can be pivoted from the lid (621) so that the edge (612) of the opening of the cover (61) can rest on the lid (621) and wherein said method further comprises, between said steps of moving the protective cover (61) and applying force on the protective cover (61) for pivoting the lid, a step of pivoting (PIV61) the protective cover (61) to bring the edge (612) of the opening of the protective cover (61) to rest on the lid (621).

20. A process according to claim 18, in which the process also comprises, after the step in which the protective cover (1; 61) is moved, a step of pulling off a sealing strip (5) affixed to the edges of a slot (20) defined between the lid (21; 621) and the first hollow body (3, 23).

21. A process according to claim 18, in which the process also comprises a step of applying a pulling or twisting force on the lid (21; 632) and/or on the protective cover (1; 61) to thereby separate the lid (21; 621) from the hollow body (3, 23).

* * * * *